(12) United States Patent
Johnson

(10) Patent No.: US 7,159,239 B2
(45) Date of Patent: Jan. 2, 2007

(54) SYSTEM TO MONITOR, DETECT AND ANALYZE CHEMICAL, RADIATION AND/OR BIOLOGICAL THREATS

(76) Inventor: R. Brent Johnson, 111 W. 5th St., Suite 300, Tulsa, OK (US) 74103

( * ) Notice: Subject to any disclaimer, the term of this patent is extended or adjusted under 35 U.S.C. 154(b) by 695 days.

(21) Appl. No.: 10/426,343

(22) Filed: Apr. 30, 2003

(65) Prior Publication Data

US 2005/0078004 A1    Apr. 14, 2005

Related U.S. Application Data

(60) Provisional application No. 60/376,866, filed on May 1, 2002.

(51) Int. Cl.
*G06F 9/24* (2006.01)
(52) U.S. Cl. .......................... 726/4; 713/193; 713/168
(58) Field of Classification Search ................ 713/136, 713/193, 168; 726/4
See application file for complete search history.

(56) References Cited

U.S. PATENT DOCUMENTS

| | | | | |
|---|---|---|---|---|
| 4,752,226 A | * | 6/1988 | Akers et al. ................. | 434/11 |
| 4,906,440 A | * | 3/1990 | Kolesar, Jr. ................. | 422/98 |
| 5,014,225 A | * | 5/1991 | Vidaver et al. .............. | 702/19 |
| 5,523,746 A | * | 6/1996 | Gallagher ................... | 340/5.61 |
| 5,970,149 A | | 10/1999 | Johnson ...................... | 380/49 |
| 6,275,855 B1 | | 8/2001 | Johnson ...................... | 709/224 |

OTHER PUBLICATIONS

The New York Times, "U.S. is Deploying A Monitor System For Germ Attacks" by Judith Miller, Jan. 22, 2003.

"Biosensors and Other Medical and Environmental Probes", by K. Bruce Jacobson, found at http://www.ornl.gov/ORNLReview/rev29_3/text/biosens.htm, pp. 1 through 18.

"Biosensors", found at http://www.drexel.edu/academics/coe/ce/web_books/EngBio/Hidden/sensr.

"An Introduction To Biosensors", by Craig Pohan and Matt Armstrong at Rensselaer Polytechnic Institute (c) 1995, found at http://www.eng.rpi.edu/dept/chem-eng/Biotech-Environ/BIOSEN2/biosensor.html.

"What are Biosensors?", found at http://www.sbu.ac.uk/biology/enztech/biosensors.html, pp. 1 through 4, last updated by Martin Chaplin on Jan. 17, 2002.

"OSU Sniffing Out Bioterrorism", by Omer Gillham, Tulsa World, Mar. 13, 2003.

"State Yields Weapon in Terrorism Battle", by Michael Bratcher, The Daily Oklahoman, Jun. 29, 2002.

"Detecting and Providing Advanced Warnings of Biological, Chemical and Radiation Threats", A Symposium Proposing Security Initiatives Conducted By Public and Private Partners within Oklahoma, Jun. 28, 2002.

\* cited by examiner

*Primary Examiner*—Thomas R. Peeso
(74) *Attorney, Agent, or Firm*—Head, Johnson & Kachigian

(57) ABSTRACT

A system to monitor, detect and analyze chemical, radiation and/or biological threats. The system includes a plurality of sensors, wherein each sensor gathers data on chemical, radiation or biological agents. A central processing unit is in communication with sensors analyzes sensor collected data. A transmission system transmits data in the form of alerts from each central processing unit by secure, encrypted packets over a network.

7 Claims, 2 Drawing Sheets

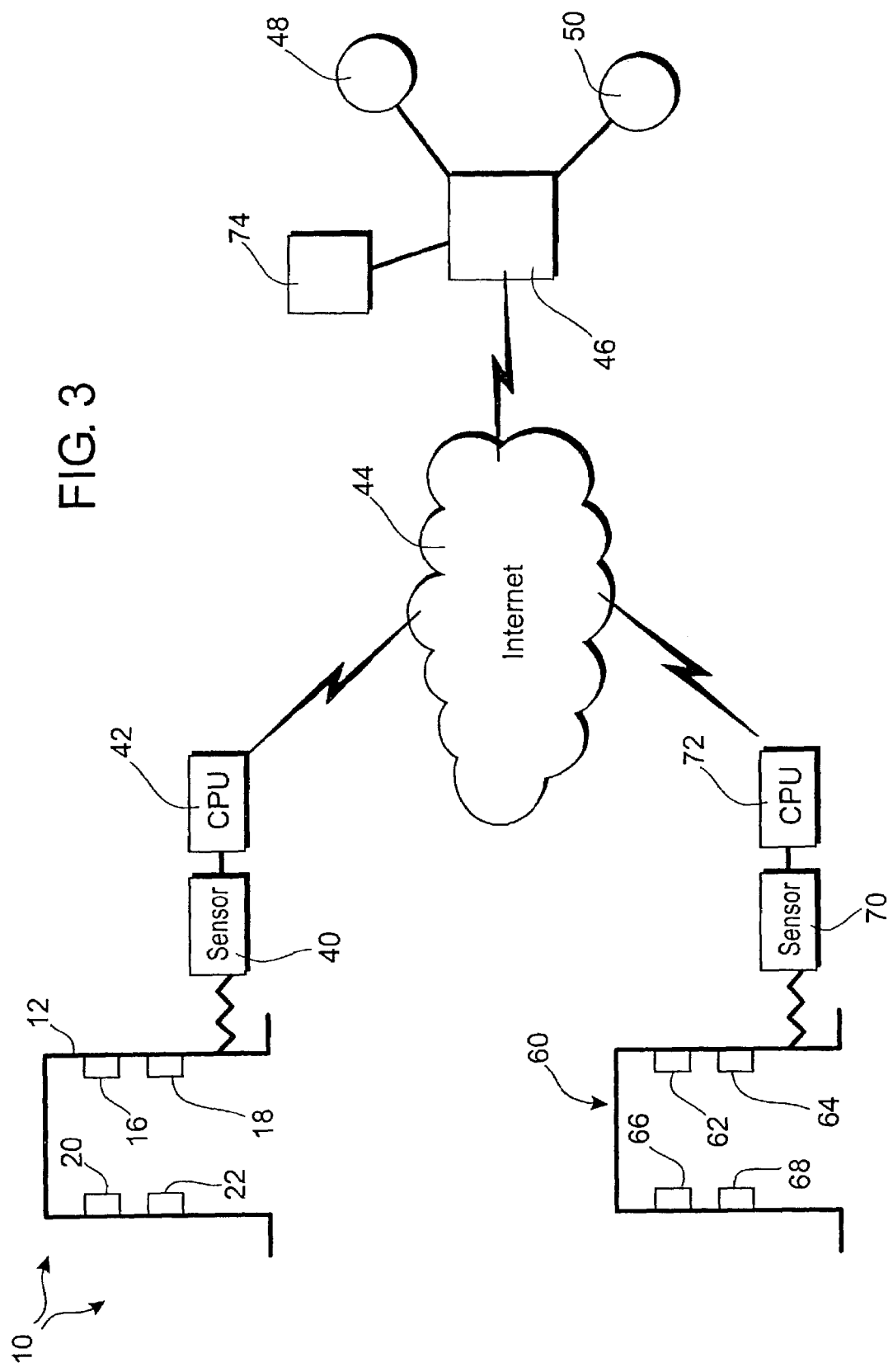

Figure 1:
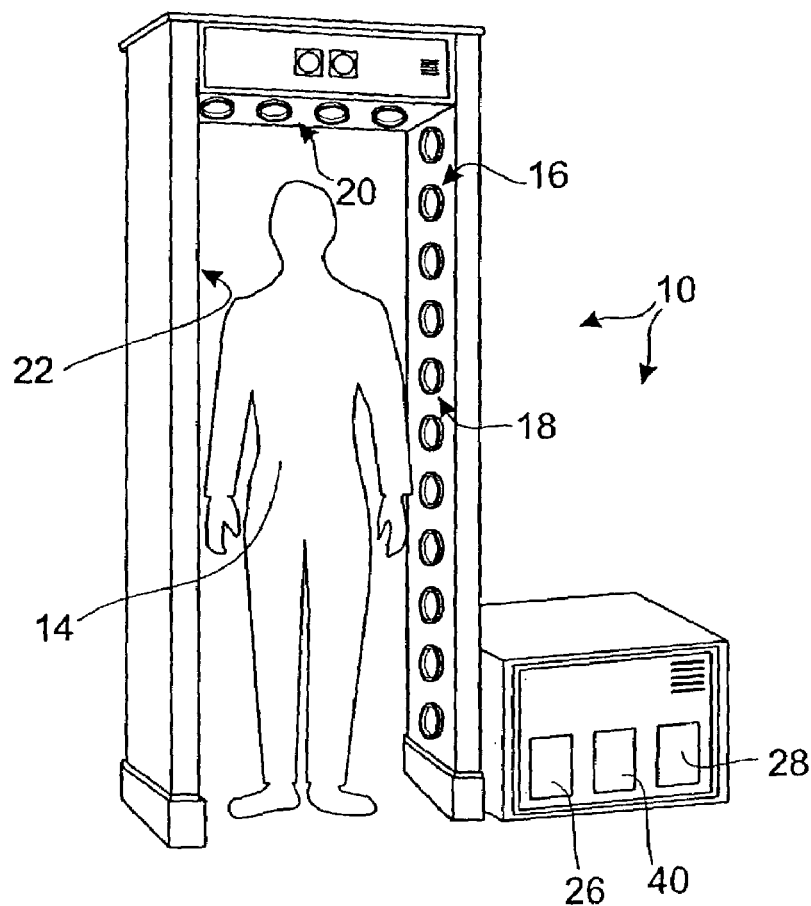
Figure 2:
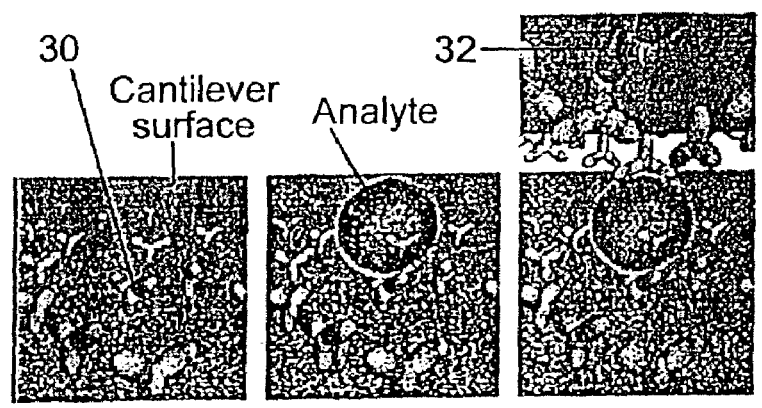

SYSTEM TO MONITOR, DETECT AND ANALYZE CHEMICAL, RADIATION AND/OR BIOLOGICAL THREATS

CROSS-REFERENCED TO RELATED APPLICATIONS

Priority is claimed from provisional application U.S. Patent Application Ser. No. 60/376,866 filed on May 1, 2002, and incorporated by reference herein.

BACKGROUND OF THE INVENTION

1. Field of the Invention

The present invention relates to a system and process to monitor, detect and analyze chemical, biological and/or radiation threats in a secure environment.

2. Prior Art

There is widespread concern about deliberate use of chemicals, radiation and biological agents. Concern about the deliberate use of disease agents includes anthrax (which can be spread by inhaled spores), small pox, pneumonia, plague, tularemia, and botulism. For example, varida, the causative agent of smallpox, is highly infectious and transmitted aerially. While many of these agents have vaccines or treatments, they do not exist in quantities that might be needed and may not be located where an outbreak were to occur.

An intentional release of a chemical, radiation or biological agent may take several days or weeks to become apparent. Suspicions may emerge only once patients begin appearing in healthcare facilities or emergency rooms with unusual symptoms or diseases.

Increasingly, it is necessary for government authorities and health care providers to be alert to illness patterns and diagnostic clues that might indicate a disease outbreak associated with an intentional release of biological or chemical agent, as well as those that occur naturally. It is desirable to quickly identify the type or nature of a chemical or biological event and implement a planned response.

Chemical warfare is the intentional use of chemicals to cause disease and death in humans, livestock and crops. Biological warfare is the intentional use of micro-organisms and their toxins to produce disease and death in humans, livestock and crops. The attraction of bioweapons in war, and for use in terrorist attacks is attributed to easy access to a wide range of disease-producing biological agents, to their low production costs, to their non-detection by routine security systems and to their easy transportation from one place to another.

Identifying biological or chemical agents via lab testing is both time-consuming and costly.

There remains a need to develop monitoring and detection systems that can gather and analyze data from multiple locations quickly.

Accordingly, it is a principal object and purpose of the present invention to develop high-throughput, reliable real-time detection systems at a low cost.

It is a further object and purpose of the present invention to correlate multiple sources of data at a central site in order to interpret and analyze sources of data, assess risk and eliminate false positives from the system.

It is a further object and purpose of the present invention to detect biothreats, chemical or radiation threats prior to emergence of symptoms in the general population.

It is a further object and purpose of the present invention to provide a system to monitor, detect and analyze data relating to the threats in a secure environment.

SUMMARY OF THE INVENTION

The present invention is a system and process to monitor and detect chemical, radiation, or biological diseases or agents categorized as threats. Examples of biological agents or diseases to be monitored include anthrax, botulism, plague, smallpox, tularemia, viral hemorrhagic fever, and influenza.

At least five component areas are included in the invention:
- detection of potential chemical, radiation, or biological threats,
- analysis, correlation and protection of data
- monitoring flow of people and events
- analysis of data using bioinfomatics identifying and dealing with particular agents to prepare ways to deal with biological threats
- apply risk analysis to data to determine response planning The system gathers data from multiple geographic locations. The system would gather data from each of multiple locations from multiple individuals by proximity to the individual. The system would be non-intrusive and non-invasive and would not raise privacy concerns as it would be passive to individuals in a number of ways. First, the system would not touch or contact an individual in anyway. Second, the information gathered would not identify any particular individual but would provide data or "data points" as they are gathered.

On a further level, the information gathered could be correlated with airline reservation and credit card data in order to alert passengers as to exposure and take other protective measures.

In one preferred exemplary embodiment of the invention, a biosensor or a plurality of biosensors would be mounted or co-located on a known walk-through metal detector such as those metal detectors utilized in airports, government buildings and the like. Additionally, a sensor or sensors might be mounted on an X-ray machine which scans luggage and equipment. The biosensor or biosensors would be physically mounted on the walk-through detection device so they are in close proximity with each individual as he or she passes through the walk-through detector.

Each sensor would incorporate a vacuum and thereby gather airborne specimens from the proximity of the individual to be analyzed by the sensor or sensors.

The present invention may be utilized with known sensors or new sensors to be developed. Known sensors are capable of monitoring and measuring air for chemical, viral, bacterial or radiation concentrations. Biosensors are capable of converting the response into an electrical signal. Types of biosensors include those that use enzymes as a biologically responsive material, whole cell metabolism, ligan debinding and antibody-antigen reaction.

In an enzyme response system, a biocatalytic membrane accomplishes conversion of a reactant to a product. This reaction is determined and sensed by a transducer which converts it to an electrical signal. The transducer makes use of a change accompanying the reaction such as heat output (or absorption) by the reaction (calorimetric biosensors), changes in distribution of charges causing an electrical potential to be produced (potentiometric biosensors), movement of electrons produced in a reduction oxidation reaction (amperometric biosensors), light output during the reaction or a light absorbance difference between the reactants and products (optical biosensors), or effects due to the mass of the reactants or products (piezo-electric biosensors).

In one sensor example, once the types of molecules to be detected are identified, an antibody will be generated which bind to any molecule to be detected. When a sample of air is introduced, the antibodies will bind to molecules to be identified. Magnetic microbeads may be introduced which have antibodies which bind to the molecules to be identified. The number of beads indicates the concentration. Cantilever beam force transducers detect the beads.

Unlike a standard metal detector, no visual or sound alarm would go off. Each sensor would simply gather data on particular biological information for immediate analysis. The information would be transmitted to a central location where the information would be correlated and then further analyzed.

In one example of utilization of the present invention, detection mechanisms located at various airports would gather information on instances of influenza existence. The number of instances could be detected. Information could be gathered as to how widespread the influenza epidemic was and what locations it had been spread to.

The present invention may be used to detect multiple sources and instances of biological airborne diseases and pathogens such as small pox or other diseases.

The present invention contemplates gathering data from a number of locations wherein each location transmits or sends the data to a central location. The transmitted data may be sent via an encrypted data stream to assure security. All of the data will at all times be stored and transmitted in an encrypted state.

By obtaining, correlating and analyzing data from multiple locations, various trends and other information can be developed. Through analysis and correlation, the system can eliminate false positives, which undermine the credibility of warning systems.

BRIEF DESCRIPTION OF THE DRAWINGS

FIG. 1 illustrates a simplified perspective view of a preferred embodiment incorporating the system to monitor, detect and analyze chemical, radiation and/or biological threats of the present invention;

FIG. 2 illustrates a sequential diagram of operation of one type of biological or chemical sensor that may be employed with the present invention; and FIG. 3 illustrates a diagrammatic view of one preferred arrangement illustrating the components of the system of the present invention.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

Referring to the drawings in detail, FIG. 1 illustrates one proposed embodiment deploying the present invention 10. Multiple collectors 16, 18, 20 and 22 would be located and mounted on a known walk-through metal detector 12, such as shown in FIG. 1. Each collector would include an air vacuum or be attached to an air vacuum 26 which would gather and pull in air surrounding the collector. Accordingly, as an individual 14 (shown in outline form) passed through the walk-through detector 12, air would be sampled in the immediate vicinity of the individual passing therethrough. By way of example and not by way of limitation, the collectors might be located approximately 25 to 50 cm away from the individual. The particular location would vary depending on the mounting location and depending on the sensitivity of the collector.

Each collector would be connected by a tube or passageway to a sensor 40 or sensor located nearby. Accordingly, an airborne specimen is obtained.

Once the collectors have gathered an airborne specimen or sample, the particulate matter in the specimen will be analyzed by the sensor or sensors. As the scanned for information is obtained, it will be transmitted to a central location.

A transmitting system central processing unit 28 will communicate information to a central information gathering location. At the central information gathering location, a monitoring system CPU validates the information, and provides for historical, or precipitating event analysis. By way of example but not limitation, the present invention might incorporate the teachings of Applicant's alert monitoring U.S. Pat. No. 6,275,855 entitled "System, Method and Article of Manufacture to Enhance Computerized Alert System Information Awareness and Facilitate Real-Time Intervention Services". The process to collect data may follow a process having a number of steps. In an initialization step, alert monitoring software will be retrieved from memory of the monitoring system CPU. Thereafter objects or events to be monitored will be determined. The monitoring system CPU will thereafter be in a ready state awaiting communication from a transmitting system CPU.

A benefit of the present invention is that it could be employed with existing metal detectors in place which would be in close proximity to those passing into and through airports and government buildings. Accordingly, the structure for deploying such a system is already in place.

A biological or chemical sensor is broadly defined as an analytical device which converts a biological response into an electrical signal. FIG. 2 illustrates a sequential diagram illustrating the operation of one type of biological or chemical sensor that might be employed with the present invention.

For each chemical, radiation or biological threat to be identified, a specific molecule or molecules will be identified.

An antibody 30 capable of recognizing a target substance will then be generated for each specific molecule and these antibodies will be bound to the sensor. A sample of entrained air will be delivered to the sensor and moved past the antibodies.

The antibodies 30 will bind to the target molecules to be identified in the solution. Thereafter, magnetic microbeads 32 will be brought past the sensor. The beads 32 have covalently bound antibodies that attach to the target molecules.

The number of beads may be counted by known cantilever beam force transducers. A tip is located at the end of a flexible cantilever which will bend in response to a magnetic force. The number of beads will indicate the concentration of the target molecules.

Other types of biosensors will employ a transducer which makes use of a physical chain accompanying the reaction. In another type of biosensor, the chemical or biological agent will generate a reaction. These may take the form of:

1. heat output (or heat absorption) by the reaction (callimetric biosensor)
2. changes in distribution of charges causing an electrical potential to be produced (potentiometric biosensor)
3. movement of electrons produced within a redox (reduction oxidation) reaction (amperometic biosensor)
4. light output during a reaction or a light absorbance difference between the reactants and products (optical biosensors) or
5. effects observed due to the mass of the reactants (piezo electric biosensor)

It will be understood that various other types of biological or chemical sensors may be employed within the scope of the present invention.

FIG. 3 illustrates a diagrammatic view of one arrangement showing the components of a system 10 to monitor, detect and analyze as set forth in the present invention. A structure such as a known metal detector 12 may have incorporated thereon a number of sensor collectors 16, 18, 20, and 22 which would be mounted thereon. Once the collectors have gathered an airborne specimen by means of a vacuum, the specimen will be analyzed by a sensor or sensors 40. The sensors 40 are replaceable so that a failure of any sensor could be addressed by simple replacement of the sensor. The sensors may be so-called "plug and play", allowing simple and robust connection with other devices by common protocols and procedures following universal standards, so that devices may be connected without additional programming. The sensor 40 will generate electronic signals or alerts which will be delivered to a transmitting or monitored central processing unit 42.

The transmitting or monitored central processing unit 42 will be connected to a network, such as the Internet 44 or standard telecommunication networks, and thereafter the data will be delivered to a central site CPU 46.

Levels of encryption are applied to all data transfer. User authentication must occur before the connection between the transmitting central processing unit and central site CPU 46 will be established. This requires the user to enter a unique ID and password, which must be approved by the target machine. The system's embedded security features inhibits the possibilities for intrusion and the willful interjection of false positives. The central site CPU 46 will, in turn, be in contact with a government agency 48 or a responder such as the Center for Disease Control.

An additional sensor collector 60 will have sensor collectors 62, 64, 66 and 68. Each of the collectors is in communication with a sensor 70. Once the collector has gathered an airborne specimen by means of a vacuum, the specimen will be analyzed. The analysis will result in sending alert data to a central processing unit 72. The central processing unit 72 is a transmitting or monitored central processing unit which is connected through the Internet 44 to a central site CPU 46. In this way, multiple sensors can gather data from multiple locations such as large office buildings and airports.

Each of the transmitting or monitored system CPUs 42 and 72 operate under the control of an operating system, such as a Linux operating system, which facilitates requests made by central site CPU software. The operating system will also have application programs in a client-server format. Various types of alert monitoring software are known to those skilled in the art and may include any number of third party offerings. Examples of such third party alert monitoring programs include, but are not limited to, Omegan, Tivoli or TNG.

One type of alert monitoring system is disclosed in Applicant's U.S. Pat. No. 6,275,855 entitled "System, Method and Article of Manufacture To Enhance Computerized Alert System Information Awareness and Facilitate Real-Time Intervention Services".

Software resident in the monitoring system CPU 46 determines objects to be monitored. The system will remain in a ready state and await communication from a monitored system CPU indicating that an alert object event has taken place. Having received an alert notification, the monitoring system next determines if the received alert is valid. If found invalid, the system advises an operator that an error has occurred and returns to await the next alert notification from a monitored system CPU.

After alert information passed from the monitored system is deemed to be valid, the system will determine if a representative icon warrants an object status modification. The modification may take the form of changing of an icon color to reflect the transition from one status state to another. By way of example and not limitation, the normal operating state might be displayed in the color green. Should a critical event occur, the icon would change the color from green to red due to the critical nature of the alert.

It will be understood herein that while the description of an alarm is made, no physical, visual or audible alarm may be made. Accordingly, the sensors operate transparently to those passing by.

Data will be correlated by the central site CPU 46 for analysis. The data will also be subject to a number of tests. For example, the data may be tested for redundancy. The data may also be checked for reasonableness.

Communication between the monitored system CPUs 42 and 72 and the monitoring system central site CPU 46 is also known to those skilled in the art. Communication can be facilitated by a network, such as the World Wide Web, or any other network configuration supporting inter-computer communication. A secure connection can be established in various ways.

For example, in one arrangement contemplated herein, the transmitting or monitored CPU 42 will retrieve a dynamic address by contacting a secure name server utilizing a unique combination ID/password which is itself encrypted. The transmitting or monitored CPU is then able to present an authorized user ID/password to a mail server and securely logon.

The central site or monitoring CPU system 46 will also obtain a dynamic address by contacting the secure name server utilizing a unique combination ID/password which is itself encrypted. The monitoring CPU is then able to present an authorized user ID/password to the mail server and log on.

Communication between the monitored CPUs 42 and 72 and the monitoring system 46 is further facilitated by way of a remote maintenance monitoring and control system 74. The purpose of the remote maintenance monitoring control system 74 is to provide for historical event data analysis and assumption of monitored system command input capabilities. Disclosure of such analysis and command technology is described in U.S. Pat. No. 5,689,637 entitled "Console Simulator Multi-console Management System and Console Management Distribution System", issued to Applicant Nov. 18, 1997 and is cited and incorporated herein by reference for purpose of providing a full detailed and enabling disclosure. Though the invention allows for remote system connectivity to a monitored system as a command console, the invention also allows for a non-console oriented response.

For example, in the event a sensor was replaced, it would be possible for the monitoring system 46 to assume command input capabilities in order to program the sensor with the desired commands.

Various objects may be monitored at the monitoring system CPU. The objects may be defined to alert event monitoring systems as input control parameters ("parm. fields") to alert event software, which is a practice known to those skilled in the art.

Relevant object information may be retained in repository in the form of a database server whereby entries associated with each monitored object are created, referenced and maintained.

It is also possible to interface with each of the transmitting system CPUs from the central site monitoring system CPU. A computer program executing within the monitoring system 46 receives computer generated alert information and, upon operator action, is capable of connecting to the transmitting system and emulating console display screens of the transmitting system as well as updates thereto. The operator at the central site may retrieve a history of activity of the display screens of the transmitting system to permit the operator to interactively analyze the transmitting system screens, to analyze dynamic event history and to input remedial actions.

In one deployment of the present invention, the system would be non-intrusive and non-invasive. For example, an individual passing a metal detector at an airport would not be specifically identified. At the same time, data gathered can be correlated and analyzed. Again by way of example, the number of airline passengers traveling from Hong Kong to San Francisco carrying influenza could be identified.

Whereas, the present invention has been described in relation to the drawings attached hereto, it should be understood that other and further modifications, apart from those shown or suggested herein, may be made within the spirit and scope of this invention.

What is claimed is:

1. A system to monitor, detect and analyze chemical, radiation or biological threats, which system comprises:
    a plurality of biosensors, wherein each said biosensor gathers data on chemical, radiation, or biological agents;
    a transmission system to transmit said data from each said biosensor via a secure, encrypted transmission wherein said transmission system retrieves a dynamic address from a secure name server using a unique ID/password combination; and
    a central site central processing unit in communication with said transmission system to collect all of said data.

2. A system to monitor, detect and analyze as set forth in claim 1 wherein said transmission system includes at least one transmitting system central processing unit remote from said central site processing unit.

3. A system to monitor, detect and analyze as set forth in claim 1 wherein said biosensors are mounted on a walk through metal detector.

4. A system to monitor, detect and analyze as set forth in claim 1 wherein transmission system transmits data in the form of alerts and wherein said central site central processing unit has a computer program executing to receive computer generated alert information.

5. A process to monitor, detect and analyze chemical, radiation biological threats, which process comprises:
    gathering data on chosen biological or chemical agents from a plurality of biosensors;
    transmitting said data from each said biosensor via a secure, encrypted transmission, wherein said data is transmitted by a transmission system over a network; and
    receiving, decrypting and analyzing said data from said plurality of biosensors, wherein said data is received at a central site central processing unit in communication with said transmission system and wherein said transmission system retrieves a dynamic address from a secure name server using a unique ID/password combination.

6. A process as set forth in claim 5 including the additional step of mounting said biosensors on a walk through metal detector.

7. A process as set forth in claim 5 wherein said data analysis includes eliminating false positives.

* * * * *